United States Patent [19]

Bryson

[11] 4,377,399
[45] Mar. 22, 1983

[54] AIR FRESHENING DEVICE

[75] Inventor: John D. Bryson, Milwaukee, Wis.

[73] Assignee: Vaportek, Inc., Milwaukee, Wis.

[21] Appl. No.: 231,985

[22] Filed: Feb. 6, 1981

[51] Int. Cl.³ .............................................. B01F 3/04
[52] U.S. Cl. ...................................... 55/226; 55/472;
 239/57; 239/59; 261/24; 261/52; 261/102;
 261/104; 261/DIG. 65; 422/124
[58] Field of Search ................ 261/96, 102, 104, 105,
 261/DIG. 17, DIG. 65, 24, 52; 422/124;
 239/56, 57, 59, 60; 55/279, 316, 472, 226

[56] References Cited

U.S. PATENT DOCUMENTS

| 2,038,071 | 4/1936 | Wilhelm | 239/59 |
|---|---|---|---|
| 3,722,182 | 3/1973 | Gilbertson | 55/279 |
| 3,785,556 | 1/1974 | Watkins | 239/6 |
| 3,790,081 | 2/1974 | Thornton et al. | 239/59 |
| 3,885,737 | 5/1975 | Watkins | 239/34 |
| 3,923,934 | 12/1975 | Watkins | 261/104 |
| 3,936,283 | 2/1976 | Solis | 55/279 |
| 4,064,203 | 12/1977 | Cox | 261/102 |
| 4,096,994 | 6/1978 | Bryson | 239/57 |
| 4,154,251 | 5/1979 | Doyel | 422/124 |
| 4,252,547 | 2/1981 | Johnson | 55/279 |
| 4,268,285 | 5/1981 | Mason | 422/124 |
| 4,272,261 | 6/1981 | Lynch, Jr. et al. | 422/124 |

Primary Examiner—Tim R. Miles
Attorney, Agent, or Firm—Michael, Best & Friedrich

[57] ABSTRACT

Disclosed herein is an air freshening device comprising an upright housing including, adjacent the bottom thereof, an air inlet and, adjacent the top thereof, an air discharge, a fan in said housing intermediate the air inlet and the air discharge means for causing air flow through the housing, a filter, structure for removably supporting the filter in the housing intermediate the air inlet and the fan in the path of the totality of the air flow through the housing, a sleeve assembly within the housing for introducing into the air flow downstream of the filter a substance to be dispensed, which sleeve assembly is operable to releasably support the filter and includes relatively rotatable inner and outer sleeves, one of the sleeves defining an interior chamber, openings in the sleeves for affording valved access to the interior chamber in response to relative rotation between the sleeves, a coupling for releasably connecting the sleeve assembly and the housing, and a package of the substance to be dispensed located in the interior chamber.

6 Claims, 5 Drawing Figures

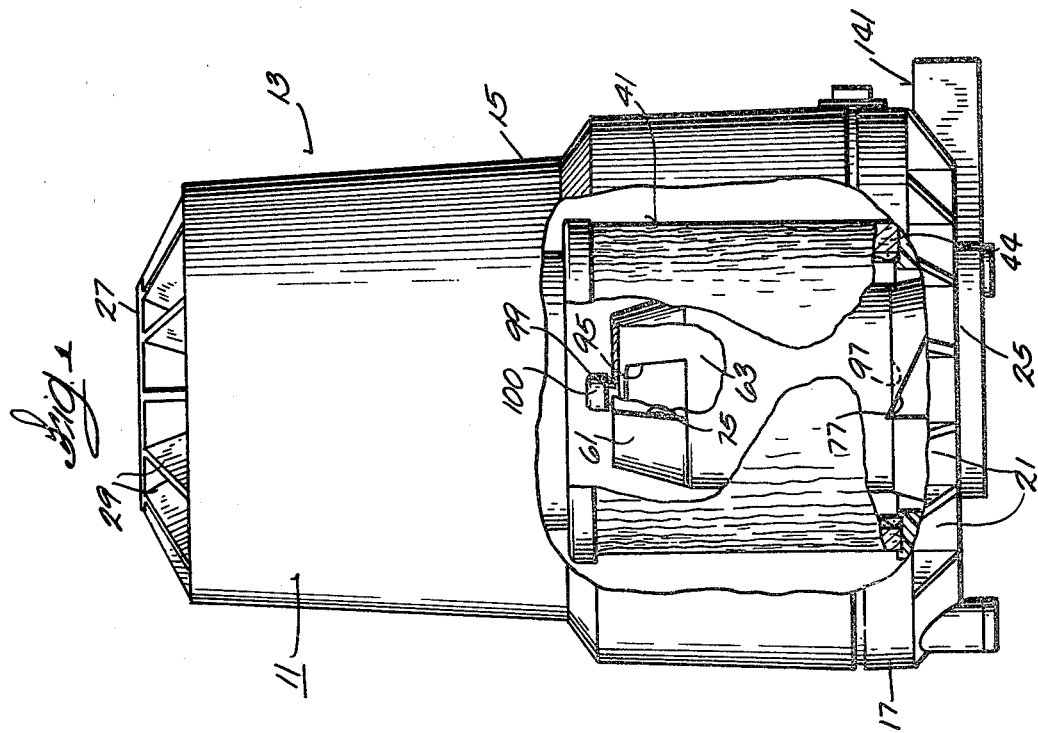
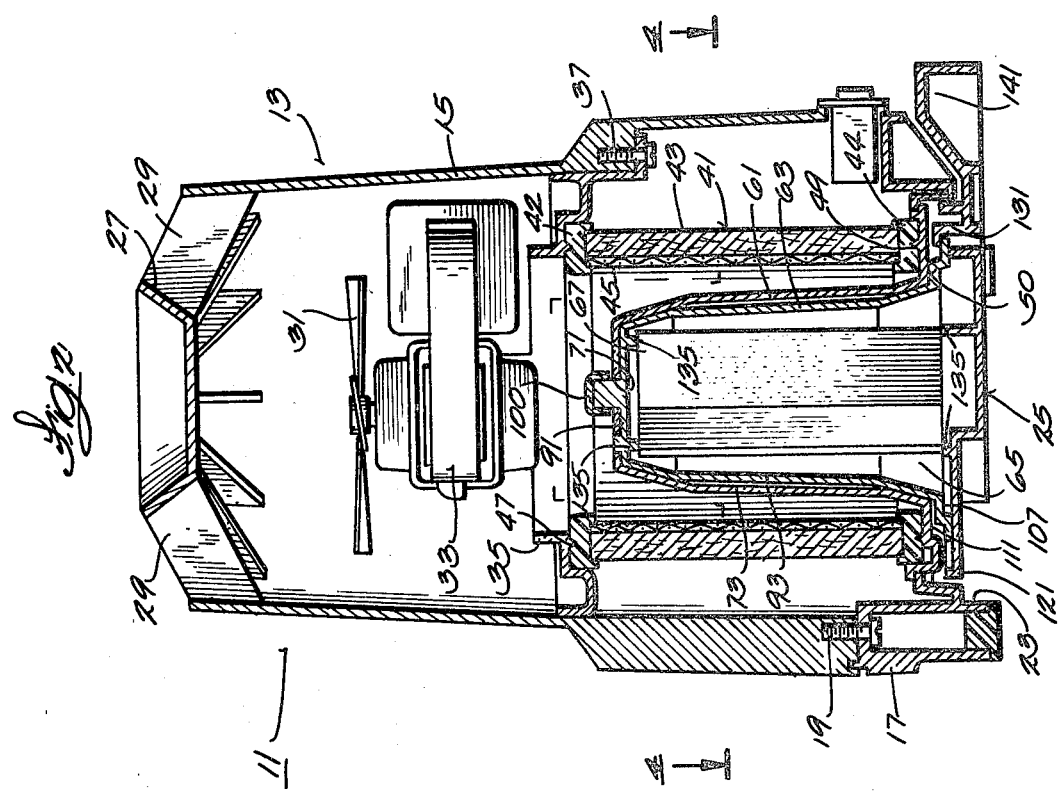

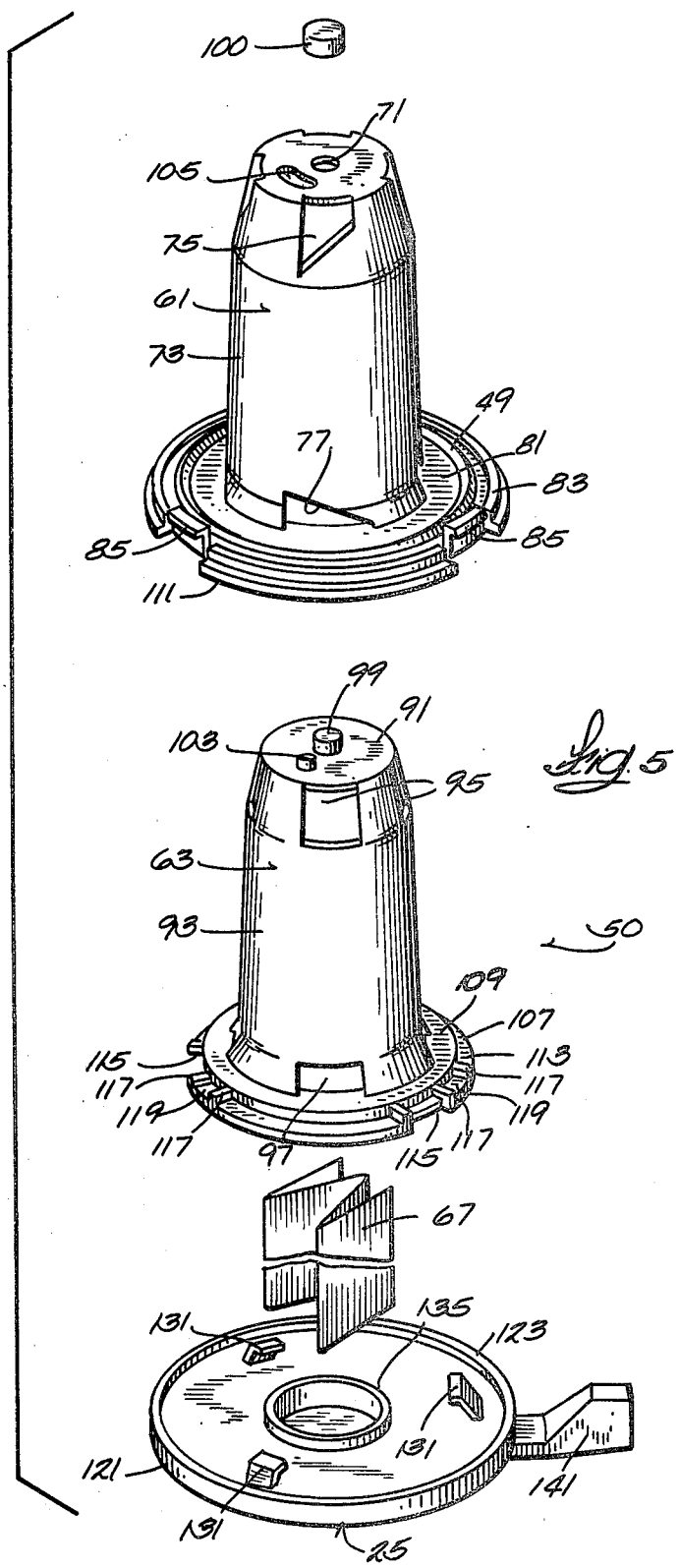

AIR FRESHENING DEVICE

BACKGROUND OF THE INVENTION

The invention relates generally to devices for dispensing into the atmosphere substances such as odorants, deodorants, insecticides, perfumes, and the like. Attention is directed to the U.S. Watkins Pat. No. 3,785,556, issued Jan. 15, 1974, and to the U.S. Watkins Pat. No. 3,885,737, issued May 27, 1975, disclosing packages which contain substances to be dispensed and which are particularly adapted for use in the freshening device disclosed herein.

Attention is also directed to the U.S. Watkins Pat. No. 3,923,934, issued Dec. 2, 1975, to the U.S. Thornton Pat. No. 3,790,081, issued Feb. 5, 1974, and to the U.S. Wilhelm Pat. No. 2,038,071 issued Apr. 21, 1936.

SUMMARY OF THE INVENTION

The invention provides an air freshening device comprising an upright housing including, adjacent the bottom thereof, air inlet means and, adjacent the top thereof, air discharge means, fan means in the housing intermediate the air inlet means and the air discharge means for causing air flow through the housing, filter means in the housing intermediate the air inlet means and the fan means, means within the housing for introducing into the air flow downstream of the filter means a substance to be dispensed, which substance introducing means comprises means defining a substantially closed chamber including valve means operable between open and closed positions, and a detachably connected member affording access to the chamber and movable to operate the valve means, means detachably connecting the means defining the chamber to the housing so as to removably support the filter means in the housing and so as to afford access to the filter means, and a package of the substance to be dispensed located in the chamber.

The invention also provides an air freshening device comprising an upright housing including, adjacent the bottom thereof, air inlet means and, adjacent the top thereof, air discharge means, fan means in the housing intermediate the air inlet means and the air discharge means for causing air flow through the housing, filter means, means for removably supporting the filter means in the housing intermediate the air inlet means and the fan means, means within the housing for introducing into the air flow downstream of the filter means a substance to be dispensed, which substance introducing means comprises a sleeve assembly constituting a part of the means for releasably supporting the filter means and including relatively rotatable inner and outer sleeves, one of which sleeves defines an interior chamber, means on the sleeves for affording valved access to the interior chamber in response to relative rotation between the sleeves, means for releasably connecting the sleeve assembly and the housing, and a package of the substance to be dispensed located in the interior chamber.

The invention also provides an air freshening device comprising an upright housing including, adjacent the bottom thereof, air inlet means and, adjacent the top thereof, air discharge means, fan means in the housing intermediate the air inlet means and the air discharge means for causing air flow through the housing, filter means in the housing intermediate the air inlet means and the fan means, and means within the housing for introducing into the air flow, downstream of the filter means, a substance to be dispensed, which substance introducing means comprises an outer sleeve having an inner end and an open outer end and having, adjacent the inner and outer ends, respective apertures, means adjacent the open end of the outer sleeve for releasably connecting the outer sleeve to the housing, an inner sleeve telescoped within the outer sleeve and having a closed inner end and an open outer end and having, adjacent the open and closed ends, respective openings means releasably connecting together the inner and outer sleeves for relative rotation between a first position with the apertures and openings substantially out of register and a second position with the apertures and the openings substantially in register, a package of the substance to be dispensed located within the inner sleeve, and closure means releasably connected to and closing the open end of the inner sleeve and including means extending exteriorly of the housing for rotatably displacing the inner sleeve relative to the outer sleeve.

In one embodiment in accordance with the invention, the filter means comprises a cylindrical filter including an outer surface communicating with the air intake means, and an inner surface communicating with the fan means, whereby air flow through the filter is from the outer surface to the inner surface.

In one embodiment in accordance with the invention, the means for introducing a substance to be dispensed is located in inwardly spaced relation from the filter inner surface, and wherein the filter and the inner and outer sleeves have coincident axes.

In one embodiment in accordance with the invention, the inner and outer sleeves include means thereon limiting relative rotation therebetween.

Other features and advantages of the embodiments of the invention will become known by reference to the following general description, claims and appended drawings.

IN THE DRAWINGS

FIG. 1 is a side elevational view, partially broken away and in section, of an air freshening device which embodies various of the features of the invention.

FIG. 2 is a sectional view, similar to FIG. 1, showing various details of the construction of the device shown in FIG. 1.

FIG. 5 is an exploded perspective view of various of the components incorporated in the device shown in FIG. 1.

Figure 3:
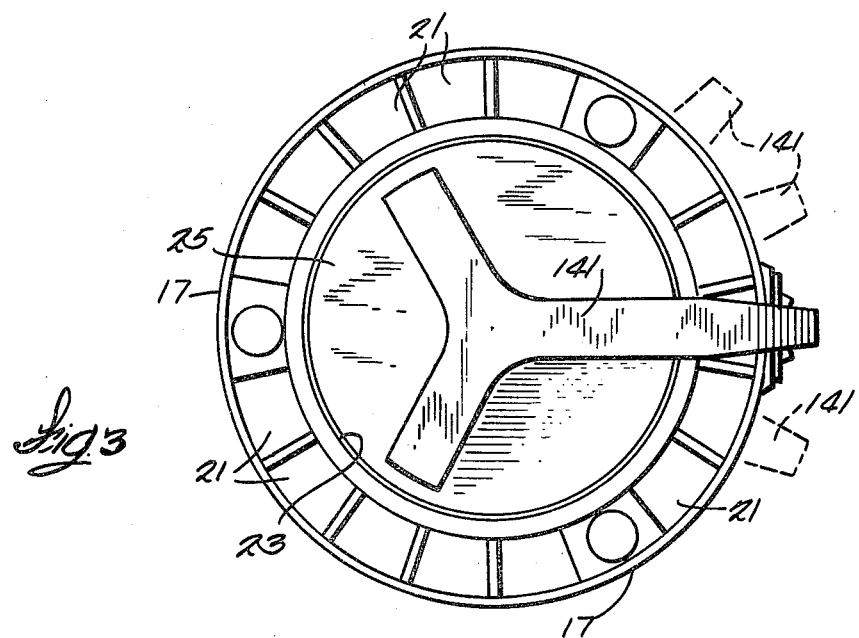
FIG. 3 is a bottom plan view of the device shown in FIG. 1.
Figure 4:
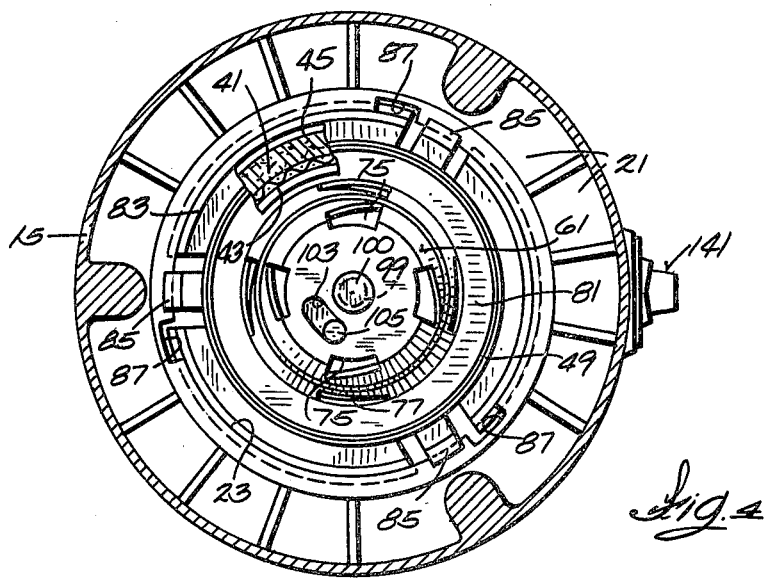
FIG. 4 is a sectional view taken along line 4 of FIG. 2.

Before explaining one embodiment of the invention in detail, it is to be understood that the invention is not limited in its application to the details of construction and the arrangement of components set forth in the following description or illustrated in the drawings. The invention is capable of other embodiments and of being practiced and carried out in various ways. Also, it is to be understood that the phraseology and terminology employed herein is for the purpose of description and should not be regarded as limiting.

GENERAL DESCRIPTION

Shown in FIGS. 1 and 2 is a dispensing device 11 which, preferably, is an air freshening device, and which includes an upright housing 13 which is preferably fabricated of plastic and which includes a hollow, generally cylindrical housing member 15 having open upper and lower ends. The housing 13 further includes a lower housing member or bottom wall 17 which is attached to the lower end of the housing member 15 by suitable means, such as screws 19, and which includes (see especially FIGS. 1 and 3) air inlet means in the form of a circular series of inlet ports 21. Inwardly of the circular series of inlet ports 21, the housing bottom wall 17 includes a central circular opening 23 which receives a closure member 25 which will be further described hereinafter.

The upper end of the hollow housing member 15 is closed by an upper housing member 27 which is suitably bonded to the housing member 15 or fabricated integrally with the housing member 15 and which includes air discharge means in the form of a circular series of air discharge ports 29.

Located interiorly of the housing 13 is fan means for causing air flow into the housing 13 through the air inlet means and out of the housing 13 through the air discharge means. While various arrangements can be employed, in the illustrated construction, such means comprises a fan 31 and a connected driving motor 33 which is carried on an annular support member 35 suitably fixed within a central part of the housing 13 by suitable means, such as screws 37.

Located within the housing 13 between the fan means and the air inlet means is filter means for filtering the totality of air flowing through the housing 13. While various arrangements can be employed, in the illustrated construction, such means comprises a cylindrical filter element 41 which includes an outer surface 43 and an inner surface 45 and which also includes an upper end support 42 and a lower end support 44 fabricated of relatively soft material such as buna rubber or plastisol, is supported, within the housing 13, with the axis thereof generally coincident with the axis of the housing member 15. Any suitable filter material can be employed, such as, for instance, a rayon-cotton non-woven material backed on an expanded metal support.

More particularly, at the upper end support 42, the filter element 41 is seated against a downwardly projecting annular, pointed rib 47 which projects from the support member 35 into the upper end support 42 of the filter element 41 to locate the filter element 41 and to provide spatial stability to the upper end of the filter element 41 and to seal or preclude air flow around the filter element 41, i.e., to prevent air flow around and not through the filter element 41.

At its lower end support 44, the end support of the filter element 41 is seated against an upwardly projecting annular, pointed rib 49 formed on a sleeve assembly 50 which is located, in part, inwardly of the filter inner surface 45, and which provides means for dispensing a substance, preferably an air freshening substance, into the air stream flowing through the housing 13. The engagement between the rib 49 and the lower end of the filter element 41 provides the same advantages and functions as the engagement of the upper rib 47 with the upper end of the filter element 41.

The sleeve assembly 50 is releasably connected to the lower housing member or bottom wall 17 by suitable means, preferably in the form of a bayonnet type connection which will be disclosed in greater detail hereinafter. The sleeve assembly 50 comprises (see especially FIG. 5) an outer sleeve 61 which is open at its lower end, an inner sleeve 63 which has a hollow interior, which is closed at its top end, which is open at its bottom end, and which extends within the outer sleeve 61 for rotation relative thereto, and the bottom closure member 25 which is releasably connected to the inner sleeve 63 to close the open bottom thereof so as to form a compartment or chamber 65. Located within the compartment 65 is a package 67 of material or substance to be introduced into the air stream. In addition, the inner and outer sleeves 61 and 63 are releasably connected to each other to retain the sleeves in closely assembled relation while affording rotary movement therebetween.

More particularly, the outer sleeve 61 comprises a member which is of cylindrical shape, which includes, at the top, a central aperture 71, which is open at the bottom, and which also includes an annular side wall 73 having, adjacent the top, one or more upper apertures 75 and having, adjacent the bottom, one or more lower apertures 77.

In addition, the outer sleeve 61 includes, at the lower end thereof, a radially outwardly extending lower flange 81. The flange 81 includes a radially inner, upper ring which constitutes the rib 49 previously mentioned, and a radially outer upper ring 83 interrupted by a plurality of fingers 85 forming a part of a suitable means releasably connecting the outer sleeve 61 to the lower housing member or bottom wall 17. In this last regard, the opening 23 in the bottom wall 17 is provided, along the margin thereof, with a series of notches 87 equal in number and spacing to the fingers 85 to permit insertion of the fingers 85 into the notches 87 and rotation of the outer sleeve 61 relative to the bottom wall 17 so as to engage the fingers 85 with the inside surface of the bottom wall 17 and thereby provide a releasable bayonnet type engagement between the outer sleeve 61 and the housing 13.

The inner sleeve 63 is also generally cylindrical in shape and is telescopically located in closely-fitting relationship within the outer sleeve 61. The inner sleeve 63 includes a closed top wall 91, is open at the bottom, and includes an annular side wall 93 having, adjacent the top thereof, one or more upper openings 95 and having, adjacent the bottom thereof, one or more lower openings 97.

Extending upwardly from the inner sleeve top wall 91 is a stud 99 which extends through the central aperture 71 in the top of the outer sleeve 61 and which cooperates with a cap 100 which is fabricated of resilient material, such as rubber, and which is releasably attachable to the extending end of the stud 99 to prevent disassembly of the inner sleeve 63 and the outer sleeve 61 from closely interfitting assembly, while permitting relative rotation therebetween.

In this last regard, the inner sleeve 63 is rotatable relative to the outer sleeve 61 between a first position in which the apertures 75 and 77 of the outer sleeve 61 and the openings 95 and 97 of the inner sleeve 63 are substantially out of register, so as to prevent air flow into or from the interior chamber 65 provided within the inner sleeve 63, and a second position in which the apertures 75 and 77 and openings 95 and 97 are substantially in register, so as to permit air flow into and out of the inner sleeve chamber 65.

The upper and lower apertures 75 and 77 and the upper and lower openings 95 and 97, together with the relative rotatability of the inner sleeve 63 and outer sleeve 61 provide valve means for the interior chamber or compartment.

Means are provided for limiting relative rotation between the inner and outer sleeves 61 and 63. While various arrangements can be employed, in the illustrated construction, such means comprises a pin or stud 103 extending upwardly from the inner sleeve top wall 91 and into an arcuate elongated slot 105 formed in the top wall of the outer sleeve 61.

At its lower end, the inner sleeve 63 includes an outwardly extending flange 107 which includes an inner, annular upper surface 109 adapted to engage the bottom surface 111 of the outer sleeve flange 81, together with an outer annular surface 113 which is reduced in height as compared with the inner annular surface 109 and which includes, on the outer periphery thereof, a plurality of notches 115 and a plurality of pairs of radially extending ribs 117 which define sockets 119 which are located adjacent to the notches 115 and which, together with the notches 115, constitute a part of a means for releasably connecting the closure member 25 to the flange 107 of the inner sleeve 63.

The closure member 25 is a disc-like member having an outer periphery 121 adapted to be relatively snugly received in the central opening 23 in the lower housing member or bottom wall 17. The outer periphery 121 of the closure member 25 includes an upwardly extending annular lip 123 which forms a recess into which the lower flange 107 of the inner sleeve 63 is received.

Formed on the inside or upper surface of the closure member 25 is a plurality of resilient fingers 131 which are equal in number and spacing to the notches 115 in the inner sleeve flange 107 and which are adapted to pass through the notches 115 and to be engaged in the sockets 119 to releasably retain the closure member 25 and the inner sleeve 63 in assembled relation so as thereby to close the lower open end of the inner sleeve 63 and so as thereby to releasably prevent relative rotation between the closure member 25 and the inner sleeve 63.

Located within the interior chamber or compartment 65 of the inner sleeve 63 is the package 67 which contains the substance to be dispensed. Preferably the package 17 is folded in accordian or serpentine shape, as illustrated, and is such that the material within the package 67 passes through the walls of the package 67 and evaporates therefrom in response to air flow through the interior of the inner sleeve 63. One example of such a package is fully disclosed in U.S. Watkins Pat. No. 3,785,556 issued Jan. 15, 1974.

Preferably, both the under surface of the inner sleeve top wall 91 and the upper surface of the closure member 25 include inwardly projecting rings 135 which engage the ends of the accordian or serpentine shaped package 67 so as to space the package ends from the inner sleeve top wall 91 and from the upper surface of the closure member 25 and thereby facilitate air flow along the surfaces of the accordian or serpentine folded package 67.

Extending downwardly from the lower surface of the closure member 25 and radially outwardly into a position exterior to the housing 13 for manipulation by the user is a lever or arm 141 which can be employed to rotate the closure member 25 relative to the inner sleeve 63 between the sockets 119 and the notches 115 and to rotate the inner sleeve 63 relative to the outer sleeve 61 within the confines of the pin 103 and slot 105 connection and so as thereby to open and close the interior chamber 65 of the inner sleeve 63 by moving the apertures 75 and 77 and openings 95 and 97 into and out of registry with one another.

In operation, the fan 31 can be turned on to cause air to flow from the lower inlet ports 21, through the housing 13, and out the air discharge ports 29, and thus through the filter element 41. Assuming the presence of a package 67 in the chamber 65 of the inner sleeve 63, the lever 141 can be employed to rotate the inner sleeve 63 relative to the outer sleeve 61 and thereby to regulate the amount of registry between the openings 95 and 97 in the inner sleeve 63 and the apertures 75 and 77 in the outer sleeve 61.

When the apertures 75 and 77 are substantially out of register with the openings 95 and 97, i.e., closed, little if any, of the substance to be dispensed will be discharged from the inner sleeve 63. In the event the openings 95 and 97 and apertures 75 and 77 are brought into partial or full registry, air will flow into the sleeve assembly 50 at the bottom and out at the top, carrying the substance to be dispensed and introducing the substance to be dispensed into the air stream downstream from the filter element 41. It is noted that all of the air stream passes through the filter element 41 and that the location of the sleeve assembly 50 radially inwardly of the filter element 41 serves to aspirate the material to be dispensed from the sleeve assembly 50.

When it is desired to inspect or replace the package 67, the closure member 25 can be rotated relative to the inner sleeve 63 to release the closure member 25 from the inner sleeve 63 and thereby permit access to the package 67 within the inner sleeve 63.

When it is desired to inspect or replace the filter element 41, the sleeve assembly can be rotated relative to the housing 13, thereby to release the sleeve assembly 50 from the housing 13 and permit withdrawal of the sleeve assembly 50 from the lower end of the housing 13. Such withdrawal provides access to the filter element 41 for inspection and/or replacement.

Thus the sleeve assembly 50 can be removed from the housing 13 independently of opening of the interior of the sleeve assembly 50 and the interior of the sleeve assembly 50 can be opened independently of disconnection of the sleeve assembly 50 from the housing 13. Accordingly, the filter element 41 and the package 67 can be independently replaced.

Various of the features of the invention are set forth in the following claims.

I claim:

1. An air freshening device comprising an upright housing including, adjacent the bottom thereof, air inlet means and, adjacent the top thereof, air discharge means, fan means in said housing intermediate said air inlet means and said air discharge means for causing air flow through said housing, filter means in said housing intermediate said air inlet means and said fan means, means within said housing for introducing into the air flow downstream of said filter means a substance to be dispensed, said substance introducing means comprising means defining a substantially closed chamber including valve means operable between open and closed positions, a detachably connected member affording access to said chamber and movable to operate said valve means, means detachably connecting said means defining said chamber to said housing so as to removably support said filter means in said housing and so as to afford access to said filter means, and a package of the substance to be dispensed located in said chamber.

2. An air freshening device comprising an upright housing including, adjacent the bottom thereof, air inlet means and, adjacent the top thereof, air discharge means, fan means in said housing intermediate said air inlet means and said air discharge means for causing air flow through said housing, filter means, means for removably supporting said filter means in said housing intermediate said inlet means and said fan means, means within said housing for introducing into the air flow downstream of said filter means a substance to be dispensed, said substance introducing means comprising a sleeve assembly constituting a part of said means for releasably supporting said filter means and including relatively rotatable inner and outer sleeves, one of said sleeves defining an interior chamber, means on said sleeves for affording valved access to said interior chamber in response to relative rotation between said sleeves, means for releasably connecting said sleeve assembly and said housing, and a package of the substance to be dispensed located in said interior chamber.

3. An air freshening device comprising an upright housing including, adjacent the bottom thereof, air inlet means and, adjacent the top thereof, air discharge means, fan means in said housing intermediate said air inlet means and said air discharge means for causing air flow through said housing, filter means in said housing intermediate said air inlet means and said fan means, and means within said housing for introducing into the air flow, downstream of said filter means, a substance to be dispensed, said substance introducing means comprising an outer sleeve having an inner end and an open outer end and having, adjacent said inner and outer ends, respective apertures, means adjacent said open end of said outer sleeve for releasably connecting said outer sleeve to said housing, an inner sleeve telescoped within said outer sleeve and having a closed inner end, and an open end, and having, adjacent said open and closed ends, respective openings, means releasably connecting together said inner and outer sleeves for relative rotation between a first position with said apertures and said openings substantially out of register and a second position with said apertures and said openings substantially in register, a package of the substance to be dispensed located within said inner sleeve, and closure means releasably connected to and closing said open end of said inner sleeve and including means extending exteriorly of said housing for rotatably displacing said inner sleeve relative to said outer sleeve.

4. A device in accordance with any of claims 2 or 3 wherein said filter means comprises a cylindrical filter including an outer surface communicating with said air intake means, and an inner surface communicating with said fan means, whereby air flow through said filter is from said outer surface to said inner surface.

5. A device in accordance with claim 4 wherein said means for introducing a substance to be dispensed is located in inwardly spaced relation from said filter inner surface, and wherein said filter and said inner and outer sleeves have coincident axes.

6. A device in accordance with any of claims 2 or 3 wherein said inner and outer sleeves include means thereon limiting relative rotation therebetween.

* * * * *